US00PP19885P2

(12) United States Plant Patent
Hammett

(10) Patent No.: US PP19,885 P2
(45) Date of Patent: Apr. 7, 2009

(54) ***DAHLIA* PLANT NAMED 'ZONE TEN'**

(50) Latin Name: *Dahlia variabilis*
Varietal Denomination: Zone Ten

(76) Inventor: Keith Hammett, 488 C Don Buck Rd., Auckland (NZ), 1008

( * ) Notice: Subject to any disclaimer, the term of this patent is extended or adjusted under 35 U.S.C. 154(b) by 257 days.

(21) Appl. No.: 11/709,673

(22) Filed: Feb. 23, 2007

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent L Bell

(57) ABSTRACT

A new cultivar of *Dahlia* named 'ZONE TEN' that is distinguishable by upright habit, mahogany-black divided leaves, and striped star-shaped blossoms with a red halo around the disk florets. In combination these traits set 'ZONE TEN' apart from all other existing varieties of *Dahlia* known to the inventor.

2 Drawing Sheets

Genus: *DAHLIA*.
Species *variabilis*.
Denomination: 'ZONE TEN'.

BACKGROUND OF THE INVENTION

The present invention relates to a new and distinct cultivar of *dahlia* grown for use in mixed combinations, beds and the landscape. The new invention is known botanically as *Dahlia* and will be referred to hereinafter by the cultivar name 'ZONE TEN'. The specific epithet *variabilis* represents a hybrid seedling line that came from crossing various original wild species in the early 1800's, and refers to the species' wide range of inflorescence color and shapes. *Dahlia* is in the family *Compositae*. The inflorescence of 'ZONE TEN' is a "single" form blossom and exhibits a single row of ray florets surrounding a central cluster of disk florets.

'ZONE TEN' was selected as an individual seedling that resulted from deliberate cross-pollination carried out by the inventor in a cultivated area of Auckland, New Zealand. The breeding began in 2001 by crossing an individual *Dahlia variabilis* 'Scarlet Fern' (unpatented) as the female parent and an individual *Dahlia variabilis* from experimental F1 Lines as the male parent. The female parent was planted in association with *Dahlia* plants that exhibited similar characteristics. Seed was collected from the female parent and coded as 71333/01, then sown with the intention of making a selection from the seedlings that resulted.

'ZONE TEN' was selected in 2002 based on the criteria of inflorescence color and flower markings. Selection was conducted by the inventor, in Auckland, New Zealand. The unique traits that distinguish the new *Dahlia* variety named 'ZONE TEN' from other varieties of the same genus, are mahogany-black divided leaves and profusions of striped star-shaped blossoms. The new *Dahlia* named 'ZONE TEN' is distinguishable from the parents by striped blossoms with a red halo around the disk florets.

'ZONE TEN' exhibits upright habit, large mahogany-black buds, dark purple stems, and mahogany-black divided leaves. The inflorescences of 'ZONE TEN' are fragrant, showy, and striped with a red halo around the disk florets bloom in summer and fall. Cultural conditions include full sun, regular water and rich well-draining potting soil. 'ZONE TEN' is hardy to USDA Zone 8 and grows to 0.9 m. in height and 0.9 m. in width at maturity.

The first asexual reproduction of 'ZONE TEN' was conducted in 2004 in Auckland, New Zealand. The method of asexual propagation utilized was tissue culture. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'ZONE TEN'. These traits in combination distinguish 'ZONE TEN' from all other existing varieties of *Dahlia* known to the inventor. 'ZONE TEN' has not been tested under all possible conditions and phenotypic differences may be observed with variations in environmental, climatic, and cultural conditions, however, without any variance in genotype.

1. 'ZONE TEN' exhibits upright habit.
2. 'ZONE TEN' exhibits mahogany-black divided leaves.
3. 'ZONE TEN' is grown for use in mixed combinations, beds and the landscape.
4. 'ZONE TEN' exhibits large mahogany-black buds and dark purple stems.
5. 'ZONE TEN' exhibits fragrant striped star-shaped blossoms with a red halo around the disk florets.
6. 'ZONE TEN' blooms summer and fall.
7. 'ZONE TEN' grows to 0.9 m in height and 0.9 m in width at maturity.
8. 'ZONE TEN' is hardy to USDA Zone 8.

BRIEF DESCRIPTION OF THE DRAWINGS

The accompanying color drawings labeled

Figure 1:
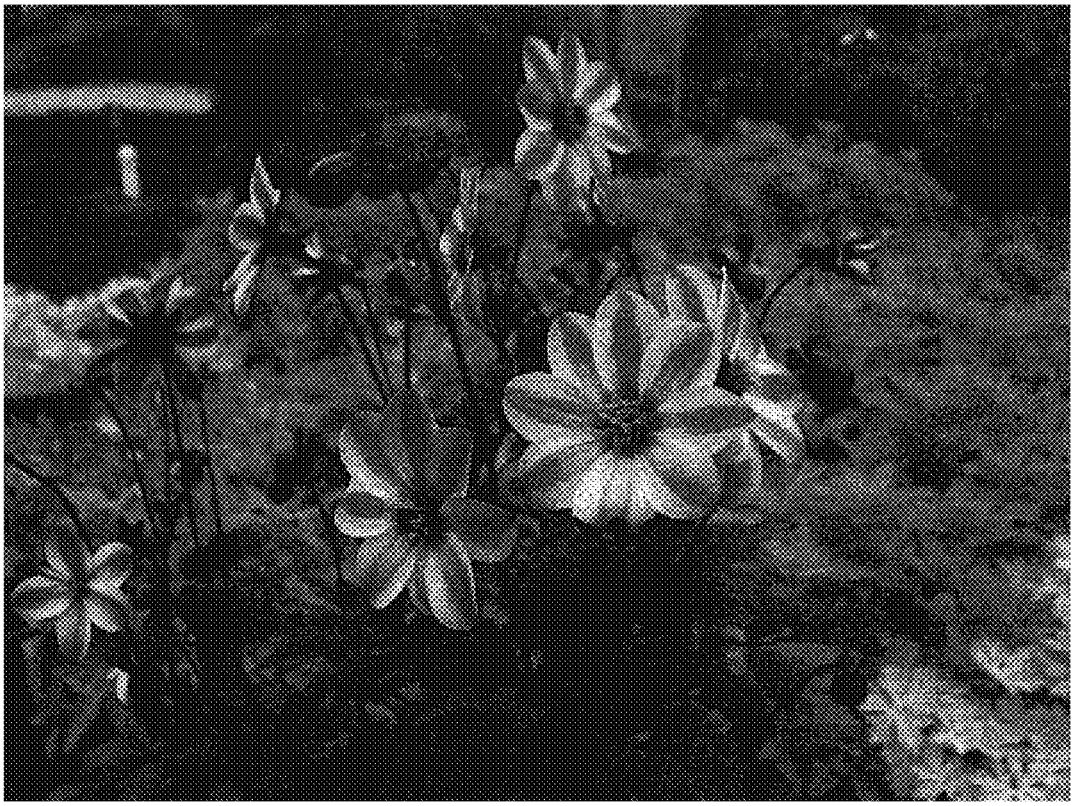
FIG. 1 and FIG. 2 illustrate the overall appearance of the new *Dahlia* cultivar named 'ZONE TEN' showing the colors as true as is reasonably possible to obtain in colored reproductions of this type. Colors in the photographs may differ from the color values cited in the detailed botanical description, which accurately describes the actual colors of the new *Dahlia* variety named 'ZONE TEN'.

The drawing labeled FIG. 1 depicts the entire plant in bloom from a side perspective.

Figure 2:
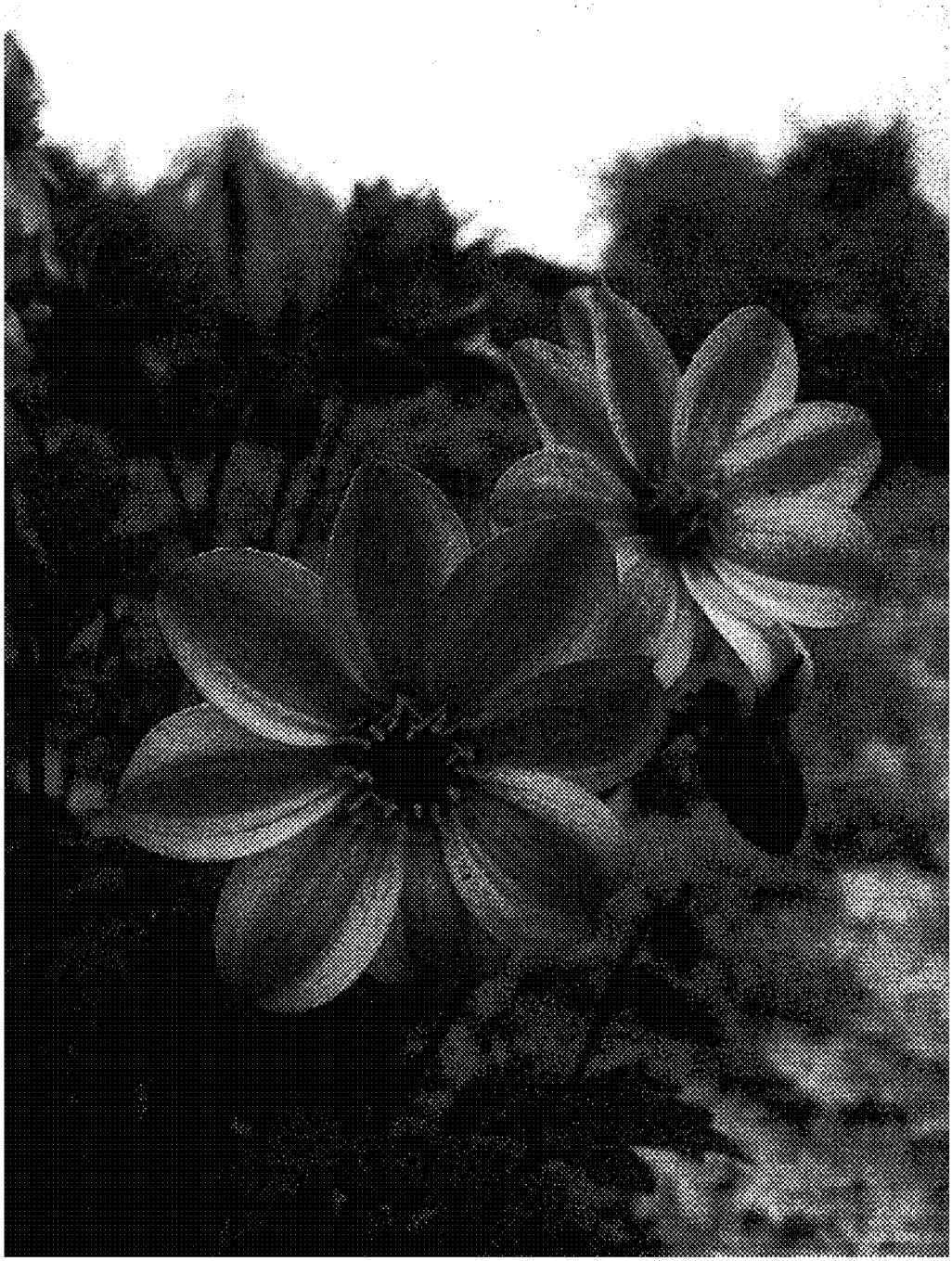

The drawing labeled FIG. 2 depicts a close-up view of the flowers. Drawings were made using conventional techniques and although inflorescence and foliage color may appear different from actual color due to light reflectance, they are as accurate as possible by conventional photography.

BOTANICAL DESCRIPTION OF THE PLANT

The following is a detailed botanical description of the new *Dahlia* cultivar named 'ZONE TEN'. Observations, measurements, values and comparisons were collected in Arroyo Grande, Calif. from 2-litre container plants. Color determinations were made in accordance with The 2001 Royal Horticultural Society Colour Chart from London England, except where general color terms of ordinary dictionary significance are used. Growing requirements are similar to the species.

Botanical classification: *Dahlia variabilis* 'ZONE TEN'.
Family: Compositae.
Genus: *DAHLIA*.
Species: *variabilis*.
Denomination: 'ZONE TEN'.
Common name: *Dahlia*.
Parentage: *Dahlia variabilis* 'ZONE TEN' is a whole seedling plant that resulted from the controlled cross-pollination of the following parents:
- *Female parent.*—*Dahlia variabilis* 'Scarlet Fern'.
- *Male parent.*—*Dahlia variabilis* of experimental F1 Lines.

Propagation method: Tissue culture.
Rooting system: Fine and fibrous.
Vigor: Vigorous.
Habit: Upright habit.
Use: For use in mixed combinations, beds and the landscape.
Type: Perennial.
Dimensions in first season: 0.6 m in height and 0.6 m in width.
Dimensions at maturity: 0.9 m in height and 0.9 m in width.
Cultural requirements: Grow in full sun with regular water, and well-draining potting soil.
Pest susceptibility: Susceptible to aphids.
Disease susceptibility: Susceptible to mildew in highly humid conditions.
Hardiness: USDA Zone 8.
Stem:
- *Color.*—N186A.
- *Dimensions.*—40 cm in length and 0.4 cm in width.
- *Shape.*—Cylindrical.
- *Surface.*—Glabrous.
- *Internode length* (*average*).—7 cm.

Foliage:
- *Type.*—Evergreen.
- *Leaf arrangement.*—Opposite.
- *Leaf division.*—Simple.
- *Margin.*—Ciliate and pinnatisect.
- *Leaf shape.*—Hastate.
- *Leaf dimensions* (*average*).—10 cm in length and 9 cm in width.
- *Leaf base.*—Attenuate.
- *Leaf apex.*—Acute.
- *Leaf venation pattern.*—Pinnate.
- *Vein color* (*abaxial and adaxial surfaces*).—N186C.
- *Leaf surfaces* (*abaxial and adaxial surfaces*).—Slightly puberulent.
- *Leaf color* (*adaxial surface*).—N186A.
- *Leaf color* (*abaxial surface*).—189A.
- *Leaf fragrance.*—None observed.
- *Presence of stipules or spines.*—None observed.
- *Leaf attachment.*—Petiolate.
- *Petiole shape.*—Sulcate.
- *Petiole dimensions.*—2.50 cm to 4 cm in length and 0.10 cm in width.
- *Petiole color.*—N186B.

Inflorescence:
- *Inflorescence type.*—Head.
- *Aspect.*—Facing upward and outward.
- *Inflorescence quantity.*—15–20 per 2-litre container plant.
- *Dimensions of inflorescence* (*average*).—7.50 cm in diameter and 3 cm in depth.
- *Inflorescence shape.*—Radiate with center disc.
- *Blooming seasons.*—Summer and fall.
- *Peduncle.*—
- *Dimensions* (*average*).—15 cm in length and 0.25 cm in diameter.
- *Shape.*—Cylindrical.
- *Surface.*—Glabrous.
- *Color.*—N186A.

Bud:
- *Shape.*—Oblate.
- *Dimensions* (*average*).—150 cm in height and 1.75 cm in diameter.
- *Surface.*—Glabrous.
- *Appearance.*—Semi-glossy.
- *Color.*—N186A.
- *Apex.*—Obtuse.
- *Base.*—Truncate.

Ray floret:
- *Dimensions* (*average*).—3 cm. in length and 2 cm. in width.
- *Form.*—Petaloid.
- *Shape.*—Oval.
- *Surface* (*adaxial and abaxial*).—Glabrous.
- *Arrangement.*—Radiate.
- *Quantity per inflorescence.*—8.
- *Apex.*—Rounded.
- *Base.*—Rounded.
- *Margin.*—Entire.
- *Color* (*adaxial and abaxial surfaces*).—72A, 70D both individually present.
- *Halo color* (*adaxial surface of ray inflorescence*).—53A.

Disk floret:
- *Dimensions.*—1.50 cm in length and 0.10 cm in width.
- *Quantity of disk florets.*—In excess of 90 disk florets per inflorescence.
- *Disk floret color.*—187A.
- *Disk florets.*—5 in number.
- *Disk florets fused or unfused.*—Fused.
- *Disk floret apex.*—Acute.
- *Disk floret surface* (*ventral and dorsal surfaces*).—Glabrous.

*Receptacle dimensions.*—0.75 cm in depth and 1.25 cm in diameter.

*Receptacle surface.*—Glabrous.

*Receptacle color.*—N186A.

Phyllary:

*Inner phyllary.*—Number: 8. Shape: Elongated ovate. Dimensions: 1.75 cm in length and 0.50 cm in width. Color (adaxial and abaxial surfaces): 59A. Texture: Scarious. Appearance: Translucent. Apex: Subacute. Base: Truncate. Margin: Entire. Surface (adaxial and abaxial): Glabrous.

*Outer phyllary.*—Number: 5. Shape: Obovate. Dimensions: 1 cm in length and 0.50 cm in width. Color (adaxial and abaxial surfaces): N186A. Form: Reflexed. Apex: Obtuse. Base: Truncate. Margin: Entire. Surface (adaxial and abaxial): Glabrous.

*Self-cleaning or persistent.*—Self-cleaning.

*Fragrance of inflorescence.*—Perfume fragrance.

Reproductive organs:

*Stamens.*—5 in number.

*Stamen length.*—6 mm. in length.

*Stamen color.*—N163D.

*Anther.*—Connate.

*Anther color.*—166A.

*Pollen.*—Present.

*Quantity of pollen.*—Large amount.

*Pollen color.*—N163D.

*Pistil.*—One present.

*Pistil length.*—9 mm. in length.

*Stigma dimension.*—6 mm in length and 6 mm in width.

*Stigma form.*—Plumose.

*Stigma color.*—23A.

*Stigma shape.*—Bifurcate.

*Ovary position.*—Inferior.

*Ovary color.*—150D.

*Ovary shape.*—Rotund.

*Ovary dimensions.*—2 mm in width and 3 mm in height.

Seed: None observed to date.

What is claimed is:

1. A new and distinct cultivar of *Dahlia* plant named 'ZONE TEN' as described and illustrated herein.

* * * * *